(12) United States Patent
Da Silva et al.

(10) Patent No.: US 8,661,650 B2
(45) Date of Patent: Mar. 4, 2014

(54) METHOD OF MAKING AN ELECTROMECHANICAL PERSONAL CARE DEVICE

(75) Inventors: Jorge M. Da Silva, Harrison, NJ (US);
Emanuel P. Morano, Totowa, NJ (US);
John Rytel, East Brunswick, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 53 days.

(21) Appl. No.: 13/246,203

(22) Filed: Sep. 27, 2011

(65) Prior Publication Data

US 2013/0074319 A1   Mar. 28, 2013

(51) Int. Cl.
*H01S 4/00* (2006.01)

(52) U.S. Cl.
USPC ............ 29/592.1; 29/595; 29/609.1; 29/831; 29/846; 73/504.04; 73/504.12; 73/504.13; 73/504.15; 73/504.16; 310/330; 310/331; 310/332; 310/340; 310/344; 333/186; 333/187; 333/188; 333/189

(58) Field of Classification Search
USPC ............ 29/592.1, 594, 595, 609.1, 831, 846; 73/504.04, 504.12–504.16; 310/330–332, 340, 344, 345; 333/186–189
See application file for complete search history.

(56) References Cited

U.S. PATENT DOCUMENTS

| | | | |
|---|---|---|---|
| 3,699,952 A | 10/1972 | Waters et al. | |
| 5,704,902 A | 1/1998 | Vandenbelt et al. | |
| 5,706,541 A * | 1/1998 | Gutelius et al. | 15/22.1 |
| 5,718,014 A * | 2/1998 | deBlois et al. | 15/22.1 |
| 6,010,264 A | 1/2000 | Scuderi et al. | |
| 6,248,007 B1 | 6/2001 | deBlois et al. | |
| 6,805,207 B2 | 10/2004 | Hagan et al. | |
| 7,313,838 B2 | 1/2008 | Long et al. | |
| 7,414,337 B2 * | 8/2008 | Wilkinson et al. | 310/50 |
| 7,565,712 B2 | 7/2009 | Long et al. | |
| 7,818,864 B2 | 10/2010 | Wilkinson et al. | |
| 7,918,862 B2 | 4/2011 | Hull, Jr. et al. | |
| 2003/0225352 A1 | 12/2003 | Eckers et al. | |
| 2005/0033112 A1 | 2/2005 | Bruton et al. | |
| 2006/0213205 A1 | 9/2006 | Reverendo | |
| 2007/0010828 A1 | 1/2007 | Eknoian et al. | |
| 2008/0208085 A1 | 8/2008 | Nan | |
| 2008/0230560 A1 | 9/2008 | Powers et al. | |
| 2009/0234182 A1 | 9/2009 | Buchholz | |
| 2009/0263174 A1 | 10/2009 | Groh et al. | |
| 2009/0263175 A1 | 10/2009 | Groh et al. | |
| 2010/0168626 A1 | 7/2010 | Gubernick et al. | |
| 2010/0222719 A1 | 9/2010 | Cowie et al. | |
| 2011/0028993 A1 | 2/2011 | Menke et al. | |
| 2013/0074307 A1 * | 3/2013 | Da Silva et al. | 29/428 |

FOREIGN PATENT DOCUMENTS

GB   2234437   2/1991

* cited by examiner

*Primary Examiner* — Paul D Kim

(57) ABSTRACT

A method of making a handheld, electromechanical device useful in mammalian body-care includes the steps of: a) forming a one-piece housing having a single opening defined by a rim; b) assembling a unitary insert; c) inserting the unitary insert through the single opening of the housing; d) removably applying a cover having an exterior surface to close the opening of the one-piece housing; and e) attaching the unitary insert to at least one of the one-piece housing and the removable cover. The rim of the one-piece housing circumscribes a rim area, and the one-piece housing has a projected area that is substantially larger than the rim area. The unitary insert is dimensioned to be insertable through the opening defined by the rim, and it has a frame having disposed thereon electromechanical elements interconnected in an electrical circuit. The cover closes off the opening of the one-piece housing.

21 Claims, 7 Drawing Sheets

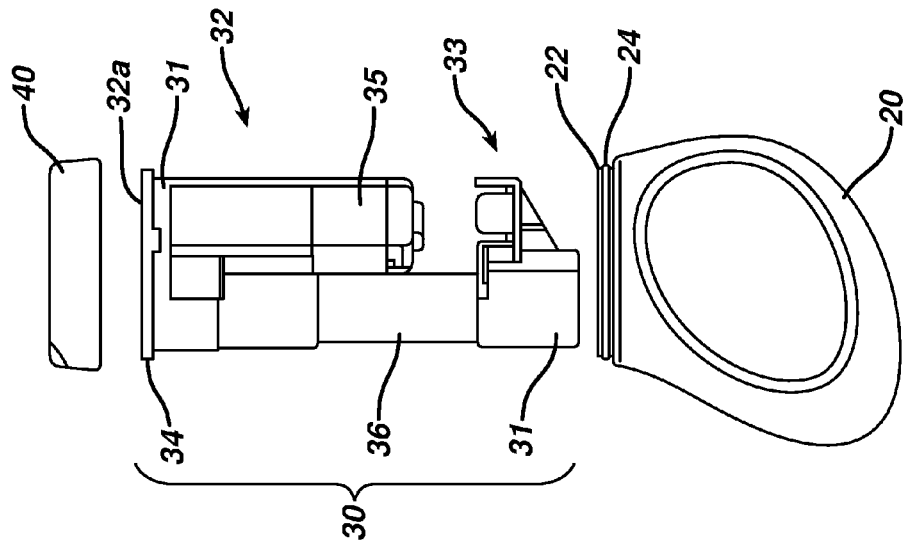
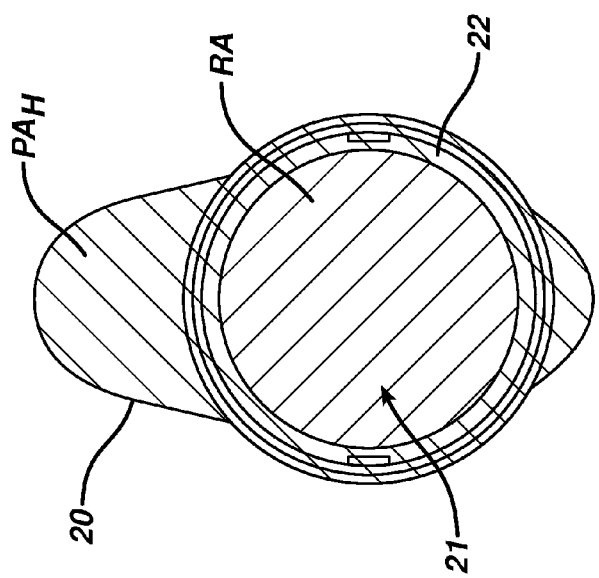
FIG. 4
FIG. 3

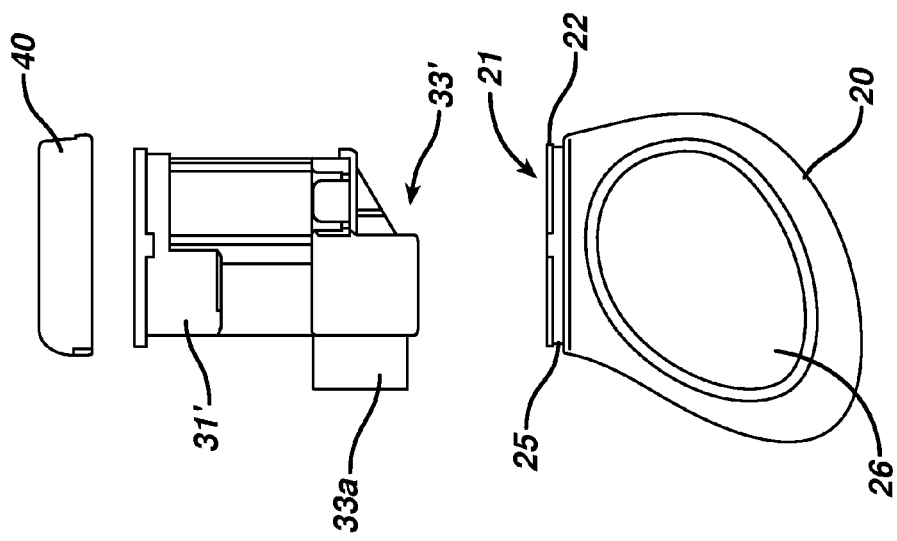
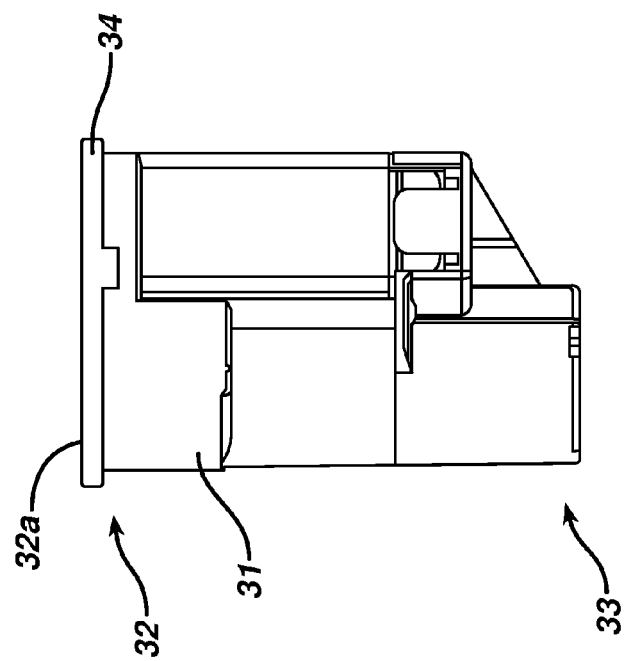

METHOD OF MAKING AN ELECTROMECHANICAL PERSONAL CARE DEVICE

FIELD OF THE INVENTION

The present invention relates to a low-cost, handheld, electromechanical personal body-care device having a one-piece housing and a unitary insert including a frame and electromechanical elements disposed thereon. The invention also relates to methods of making and assembling the devices and to kits containing interchangeable components of such devices.

BACKGROUND OF THE INVENTION

Handheld, electromechanical, personal body-care devices are known. Many of these devices have mechanisms to transmit motion, such as vibration, rotation, oscillation, and the like, to a body surface, such as a human face, elbows, and/or feet.

Hull, Jr. et al., U.S. Pat. No. 7,918,862, discloses a water-resistant device incorporating a switch assembly. This is a typical example of an injection-molded clamshell housing that includes structural features to permit electromechanical elements to be mounted on the housing. In more detail, the device includes a housing formed of a hard, lightweight plastic material, which may be formed of two portions and attached along a seam. In addition to this seam between the housing portions, additional openings for a battery compartment and power switch are formed in the housing. Each of these openings employs a water-resistant seal.

Cowie et al., US Pat. Appl. No. 2010/0222719 purports to disclose a facial care appliance having a tubular body containing electromechanical elements. The tubular body is formed of mating, inter-fitting semi-cylindrical sidewalls and has outer skins disposed thereon. Thus, this body requires numerous seams to be sealed or gasketed if it is to be used in wet environments to protect the internal electromechanical elements.

Despite the teaching of the prior art, there is a continuing need for skin care devices that provide simple and reliable manufacture, reliable protection against water damage, and potential for customization.

SUMMARY OF THE INVENTION

Therefore, we have discovered that separating the housing and the electromechanical elements of a handheld personal body-care device increases manufacturing flexibility, reduces manufacturing costs, and reduces potential for the undesired ingress of liquids.

In particular, a method of making a handheld, electromechanical device useful in mammalian body-care includes the steps of: a) forming a one-piece housing having a single opening defined by a rim; b) assembling a unitary insert; c) inserting the unitary insert through the single opening of the housing; d) removably applying a cover having an exterior surface to close the opening of the one-piece housing; and e) attaching the unitary insert to at least one of the one-piece housing and the removable cover. The rim of the one-piece housing circumscribes a rim area, and the one-piece housing has a projected area that is substantially larger than the rim area. The unitary insert is dimensioned to be insertable through the opening defined by the rim, and it has a frame having disposed thereon electromechanical elements interconnected in an electrical circuit. The cover closes off the opening of the one-piece housing.

BRIEF DESCRIPTION OF THE DRAWINGS

FIG. 3 is a top view of the housing of FIG. 1 showing the projected area of the housing.

FIG. 4 is an exploded, side elevation of the device of FIG. 1.

FIG. 5 is a detailed view of the unitary insert of FIGS. 1 and 4.

FIG. 6 is an exploded, side elevation of an alternative embodiment having a unitary insert with a modified distal end.

DETAILED DESCRIPTION OF THE PREFERRED EMBODIMENTS

A review of the prior art described above suggests that elegant, simple solutions to water resistant electromechanical personal body-care devices are still needed. In particular, plastic housings are often two-piece, injection-molded clam shell structures. This provides ease in manufacturing with structural elements extending from the interior surface of the housing that form mounting surfaces for electromechanical elements contained therein. However, as the electromechanical elements are changed during the evolution of a commercial product, either the injection mold must be modified, or there are significant structural limitations on the design evolution. Alternatively, changes in the housing must be designed in conjunction with the mounting of the electromechanical elements. In addition, mounting electromechanical elements directly on the housing provides direct pathways to transfer undesired motion to the gripping surfaces of the housing. Finally, combining multiple plastic pieces together to form a unitary housing requires additional locations to seal the structure from the possible ingress of liquids, such as water.

Therefore, we have separated the housing and the electromechanical elements to increase manufacturing flexibility, reduce manufacturing costs, and to reduce potential for the undesired ingress of liquids. In particular, we have invented a low-cost, handheld, water-resistant electromechanical, personal body-care device that has a one-piece housing and a single opening defined by a rim, a unitary insert dimensioned to be insertable through the opening, and a removable cover arranged and configured to engage the rim. The unitary insert includes a frame having disposed thereon electromechanical elements interconnected in an electrical circuit. The removable cover has an exterior surface, and it is arranged and configured to transmit at least one output of the electromechanical elements disposed within the housing.

As used herein the specification and the claims, the term "unitary" and variants thereof means a collection of parts joined to form a whole.

As used herein the specification and the claims, the term "rim" and variants thereof means the edge of a structure defining an opening, which may be circular or other geometric shape.

As used herein the specification and the claims, the term "projected area" and variants thereof means the area of the projection of a three-dimensional object onto a plane. When two or more projected areas are compared, the projection is onto the same plane.

As used herein the specification and the claims, the term "removable cover" and variants thereof relates to covers that are designed to be applied to close the opening of the one-piece housing and to be removable therefrom without undue effort and/or damage to any of the cover, unitary insert, and one-piece housing.

Figure 1:
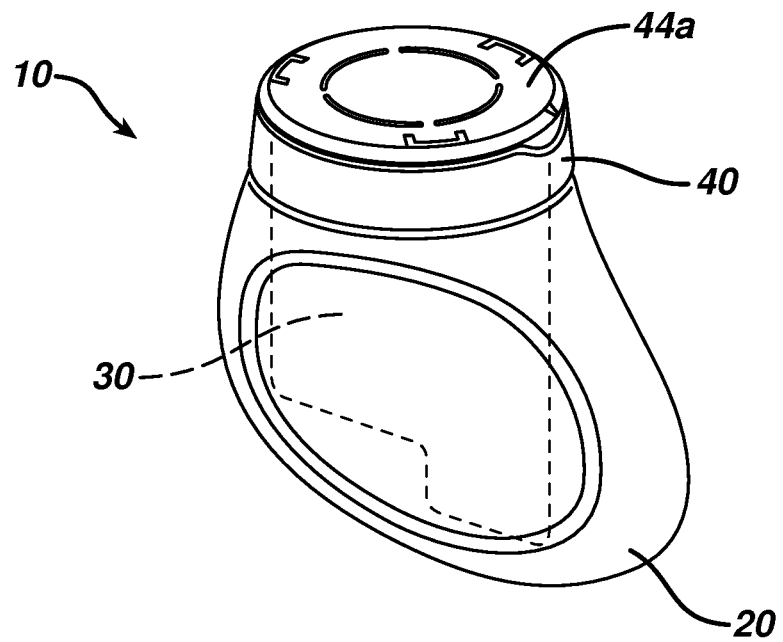
FIG. 1 is a perspective view of one embodiment of the device of the present invention.

As shown in FIG. 1, a first embodiment of the device of the present invention is a handheld, water-resistant electromechanical device 10 useful in mammalian personal body-care. The device includes a one-piece housing 20 containing a unitary insert 30 and having a cover 40. Preferably, the one-piece housing 20, the unitary insert 30, and the cover 40 are arranged and configured to resist the ingress of liquids into the device. This may be done by selective use of gaskets, as described below. Thus, the device can better resist the ingress of liquids into the device. In addition, the unitary insert 30 is attached to at least one of the one-piece housing 20 and the cover 40 to provide a more robust device.

Figure 2:
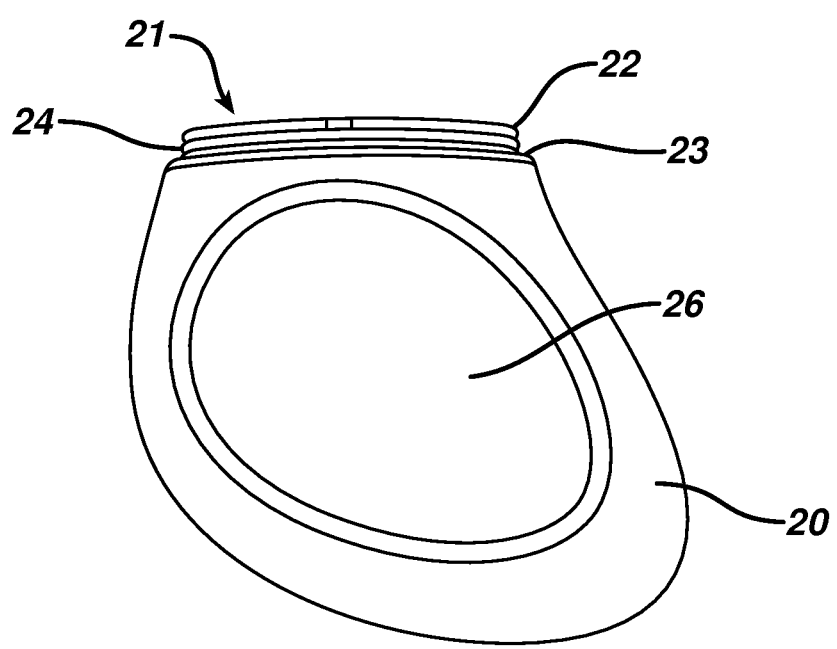
FIG. 2 is a side elevation of the housing of FIG. 1.
Figure 7:
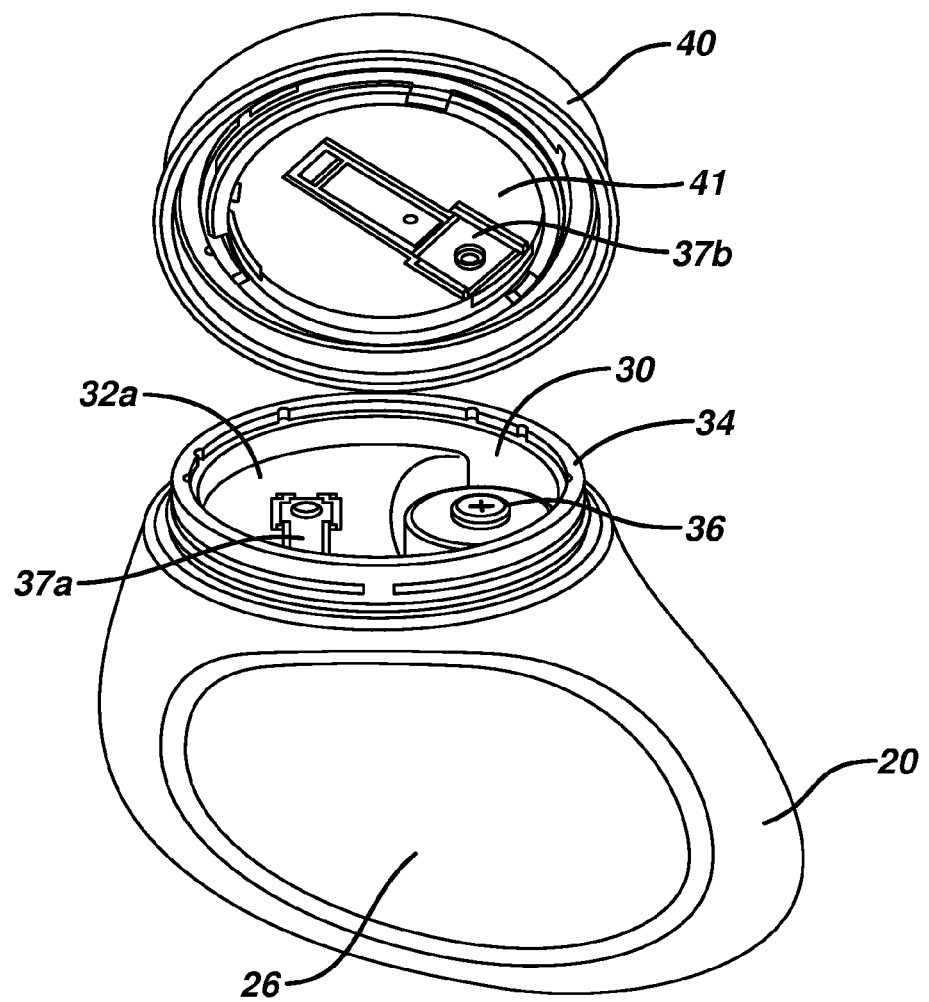
FIG. 7 is a perspective view of the cover and housing/insert of FIGS. 1-5 with the cover separated from the housing/insert and rotated to show the underside of the cover.
Figure 10:
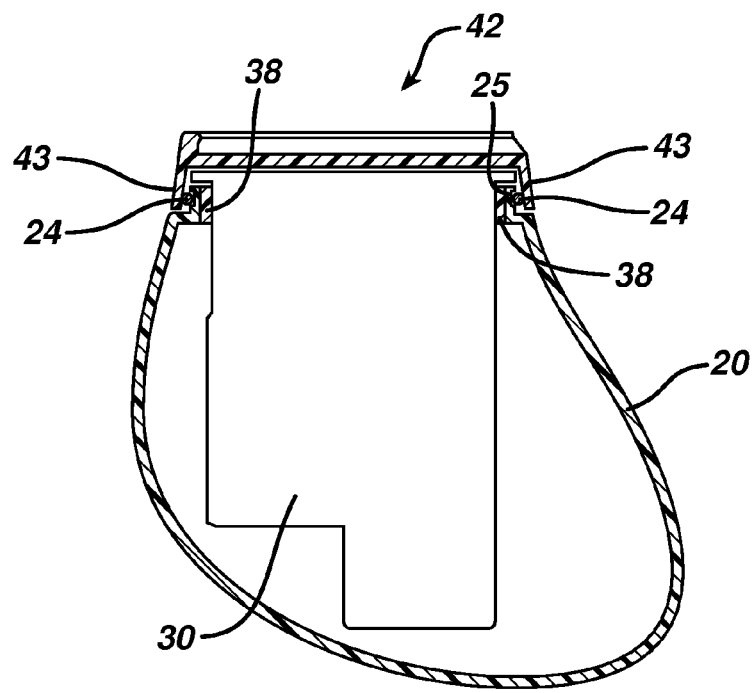
FIG. 10 is a partial cross-section of the housing and insert of an embodiment of the present invention having a gasket disposed between the insert and the housing.

As shown in FIG. 2, the one-piece housing 20 defines a volume contained by the housing, and it has a single opening 21 defined by a rim 22. The one-piece housing preferably has an ergonomic shape that facilitates holding by a human hand. The handheld electromechanical device is light-weight to prevent user fatigue during use. Preferably, the handheld, electromechanical device has a mass of less than about 450 grams; more preferably, less than about 300 g; and most preferably, less than about 150 g. The one-piece housing 20 has a substantially continuous exterior wall to provide a pleasing appearance and to eliminate the risk of poorly closed seams between housing components present in multi-part housings that can provide pathways for the ingress of liquids into the device. The single opening greatly reduces the number of and linear dimension(s) of seams in the construction of the electromechanical device. It may be desirable to provide a shoulder 23 proximate the opening 21. Thus, the rim 22 can extend from the shoulder 23 to permit the cover 40 to engage and fit over the rim 22 in this embodiment. A gasket 24 may be disposed about the rim 22. As shown in FIGS. 2 and 10, the gasket 24 is an o-ring, and it is disposed in a groove 25 dimensioned to provide an effective, sealing seat for the gasket 24 to prevent the ingress of liquids into the device 10. While a circular opening and corresponding rim are shown in FIGS. 1-5, it will be recognized that alternative geometric shapes are possible.

The one-piece housing 20 preferably has an interior surface that is substantially smoothly continuous for ease of manufacture and for improved mechanical isolation of the unitary insert 30 from the housing 20. This smooth, continuous interior surface also necessitates assembly of electromechanical elements on the frame of the unitary insert, as discussed in greater detail, below. As shown in FIG. 3, the one-piece housing 20 has a projected area $PA_H$ (shown by cross-hatching within bold outside line defining the periphery of the projection) that is substantially larger than the rim area RA (shown by opposite cross-hatching within the opening), the area circumscribed by the rim 22. In this embodiment, the projected area PA is symmetrical on opposite sides of a plane perpendicular to the rim 22, although it is not radially symmetrical about the center of the rim 22. In alternative embodiments, the projected area may be radially symmetrical about a center of the opening 21, symmetrical across multiple planes perpendicular to the rim, or it may be isotropic (having a structure independent of the direction from the center or diameter of the opening).

The outer surface of the one-piece housing may be smooth or it may have surface features, such as highlighted gripping area 26. The surface features may be formed during the formation of the one-piece housing or they may be added later. These surface features may include without limitation, texturing, coloring, information, etc. The surface features may be provided through known methods, such as by coating (e.g., printing, and/or painting), applying labels or other structures, etching, dyeing, and the like. Texturing may be slight or it may be substantial enough to be noticeable on the interior surface of the housing. The one-piece housing can be transparent in order to be able to see the internals. This is useful for using LED's internally as status indicators. Housing 20 is preferably rigid, although it may be helpful to have one or more flexible portions. Alternatively, the one-piece housing may be more flexible. The partial or complete flexibility may be useful to incorporate a switch that the user can depress by flexing the housing (same applies for the cap) or having a pump for dispensing liquids therethrough. Gaskets protect the ingress of liquids from the exterior, but in another embodiment can be used to protect liquids from exiting.

FIG. 4 shows an exploded, side elevation of the device of FIG. 1 to show the relationship between the one-piece housing 20, the unitary insert 30, and the cover 40, and FIG. 5 provides additional details of the unitary insert 30 and its constituent elements. Again, the unitary insert 30 includes a frame 31 having disposed thereon electromechanical elements interconnected in an electrical circuit. The frame 31 has a proximal portion 32 and a distal portion 33 disposed opposite thereof. A flange 34 or other attachment surface is at the proximal end 32 to attach to or to engage with the rim 22 or other portion of the housing 20 near the opening 21 to secure the unitary insert 30 to the housing 20. The electromechanical elements are mounted on or disposed within recesses in the frame 31. For example, in the embodiment shown in FIGS. 4 and 5, the insert 30 includes an electric motor 35 and a power source such as a battery 36 interconnected, e.g., with wires or other electrical conduits, in an electrical circuit. The circuit may be opened and closed by means of a switch, elements of which may be located on the cover, as discussed in further detail, below.

The unitary insert 30 is dimensioned to be insertable through the opening 21 and to be substantially contained within the one-piece housing 20. In the embodiment of FIGS. 1-5, the unitary insert 30 has a projected area $PA_I$ that is circumscribed by the rim 22 (see FIG. 4). It should be noted that this projected area does not include any portion of the mounting flange 34 that is to be secured to the rim 22 through an interference fit or by overlapping with a portion of the rim 22. In other words, the unitary insert 30 is insertable into the opening 21 with a single, linear motion without interference. In an alternative embodiment shown in FIG. 6, the unitary insert 30' has a projected area $PA_I'$ that extends outside of the opening due to a lateral extension of a distal portion 33'. This unitary insert 30' is insertable into the opening 21 by first inserting the distal portion 33' through the opening 21, pivoting the unitary insert 30' to align a remaining portion of the unitary insert that has a projected area that is circumscribed by the rim, and inserting the remaining portion of the unitary insert 30' through the rim 21.

The removable cover 40 engages the rim 22 to close the opening 21. In the embodiment of FIGS. 1-5, the removable cover 40 is a cap that is arranged and configured for removable engagement over the rim 22. The cap also engages the gasket 24 disposed about the rim 22 to prevent the ingress of liquids into the device 10. This sealing engagement protects the electromechanical elements from damage, including short-circuiting, that water or other liquids may cause if it were to penetrate into the interior of the housing 20. In the embodiment of FIGS. 1-5 and 7 and also in the embodiment of FIG. 10, discussed in greater detail, below, the cap has an inner surface 41 disposed toward the unitary insert 30 that closes the opening 21, and an exterior surface 42 disposed away from the opening 21. In addition, the cap has sidewalls 43 that encircle the rim 22 and engage the gasket 24. The exterior surface 42 may itself be a body-care surface, or it may be a platform or other structure on which optional, body-care elements, 44 may be disposed, either directly on the exterior surface 42 or through an optional coupler 44a such as disclosed in commonly assigned, Hull, U.S. Ser. No. 12/770, 994, filed Apr. 30, 2010. Such optional, body-care element may be applied directly on the optional coupler 44a or onto the exterior surface, or there may be an attachment mechanism, such as a hook-and-loop system, or adhesives, clamps, snaps, and the like.

In the preferred embodiment show in FIGS. 1-5, the cover cooperates with the insert to form a switch. This is shown in more detail in FIG. 7. The unitary insert 30 has a first electrical conductor 37a disposed on its proximal surface 32a, and the inner surface 41 of the cap has a second electrical conductor 37b. The cap is preferably engaged with the rim 22 via a bayonet connector mechanism with one or more pins disposed on the frame and matching "L" slots disposed in the inner walls 43 of the cap. The cap and/or rim are formed of a sufficiently resilient material to permit the cap and rim to be removable locked together. In this embodiment, the "L" slot is extended to permit the cap to rotate between (1) an "on" position in which the second electrical conductor 37b on the cap connects the first electrical conductor 37a disposed on the proximal surface 32a of the unitary insert 30 and the battery 36 to close the electrical circuit and (2) an "off" position in which the second electrical conductor 37b on the cap is rotated to break the electrical circuit by disengaging either or both of the first electrical conductor 37a on the unitary insert 30 and battery 36.

Although the previous paragraph described a bayonet coupling between the cover 40 and insert 30, the elements of the bayonet coupling such as the pins and slots can be located on combinations of housing 20, the unitary insert 30, and the cover 40.

Another embodiment may replace the rotating switch formed by the combination of the cover 40 and the insert 30 with a push-button switch operated by flexing the housing and/or cover.

Figure 8:
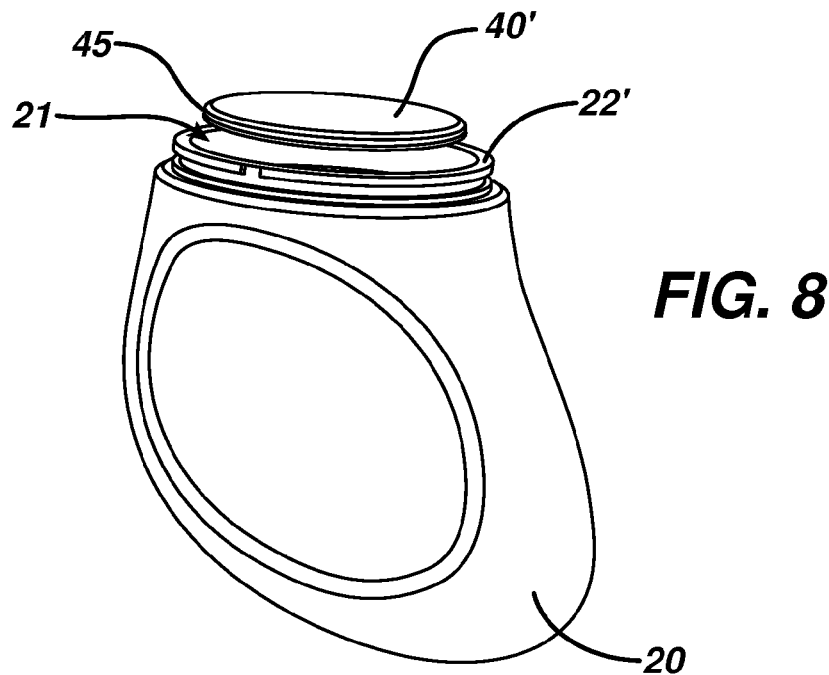
FIG. 8 is an exploded, perspective view of the cover and housing of an embodiment of the present invention having a cover in the form of a plug.

In an alternative embodiment shown in FIG. 8, the cover is a plug 40' that is arranged and configured for removable engagement within the rim 22'. A gasket 45 such as an o-ring may be disposed about the plug 40'. Again, the o-ring may be disposed in a groove dimensioned to provide an effective, sealing seat for the gasket 45 to prevent the ingress of liquids into the device 10.

Figure 9:
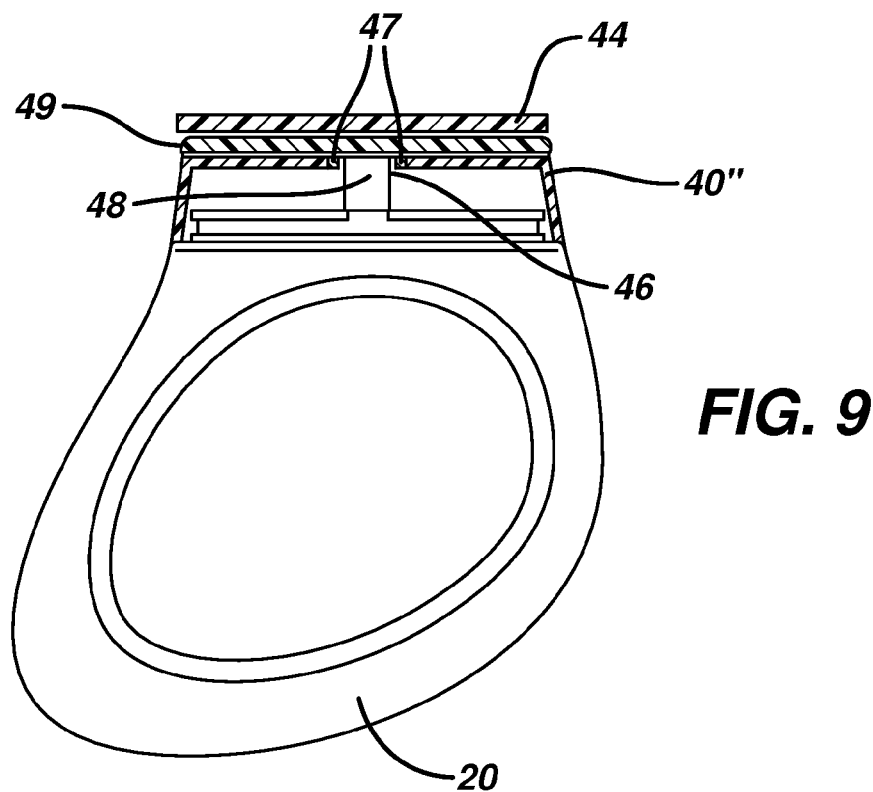
FIG. 9 is a partial cross-section of an embodiment of the present invention having a shaft disposed through the cover.

In a further alternative embodiment shown in FIG. 9, the cover 40" may have an aperture 46 having a shaft gasket 47 and a moveable shaft 48 disposed therein, and wherein the moveable shaft 48 is operatively connected to the motor 35 mounted on the insert to transfer motion from the motor 35 to a moving platform 49 having body-care element 44 disposed thereon outside of the housing 20. Thus, the body-care element 44 may rotate or oscillate against the user's skin. Other motion outputs are also possible. For example, cams, slides, and/or other translational mechanisms may interact with the moving platform 49.

As mentioned above, it is desirable to construct the body-care device 10 to resist the ingress of liquids into the device to avoid damage to the electrical components contained therein. Thus, the housing 20 sealingly engages with at least one of the unitary insert 30 and cover 40. The use of one or more gaskets 24, 45 between the cover 40 and the housing 20 are described above. In addition or in place of such gaskets, it may be desirable to seal the connection between the housing 20 and the unitary insert 30. Thus, an appropriate gasket 38 may be disposed between the housing 20 and the unitary insert 30, as shown in FIG. 10. This gasket 38 may simply resist the ingress of liquids into the interior of the housing 20, or it may also act as a damping member to dampen movement generated by the electromechanical elements disposed on the frame 31 and isolate it from transfer to the housing 20. However, if one determines that water-resistance is not critical to the operation of the device, one or more of the gaskets can be eliminated.

As can be seen in a review of the foregoing paragraphs, cover 40 is arranged and configured to transmit at least one output of the electromechanical elements disposed within the housing. For example, in the embodiment of FIGS. 1-5, vibratory motions from the insert 30 may be transferred through the cover 40 to the exterior surface 42. In the embodiment of FIG. 9, rotating or oscillating motion from the insert may be transferred through the cover 40" via moveable shaft 48 to a skin-contacting element 48. In the embodiment of FIG. 10, the vibratory motions from the insert 30 may be isolated from the housing 20 and transferred directly to a skin-contacting element 48.

As discussed above, the one-piece housing 20 defines a volume contained by the housing. When the opening 21 is closed by the cover 40, the volume contained by the one-piece housing is at least about 60% of the total volume contained by the one-piece housing 20 and the cover 40. Preferably, the volume contained by the one-piece housing is at least about 80%, and more preferably at least about 90% of the total volume contained by the one-piece housing 20 and the cover 40.

The device of the present invention is made by forming a one-piece housing, assembling a unitary insert, inserting the unitary insert into the housing, attaching the unitary insert to the one-piece housing, and removably applying a cover to the housing. Again, the one-piece housing defines a volume and has a single opening defined by a rim. The housing also has a substantially continuous exterior wall, and it has a projected area that is substantially larger than the rim. Preferably, the housing has a shoulder, and the rim extends above the shoulder. The rim may also have a gasket disposed thereabout. Thus, the device may be made by forming a one-piece housing having an opening defined by a rim and arranging a gasket about the rim.

Figure 11:
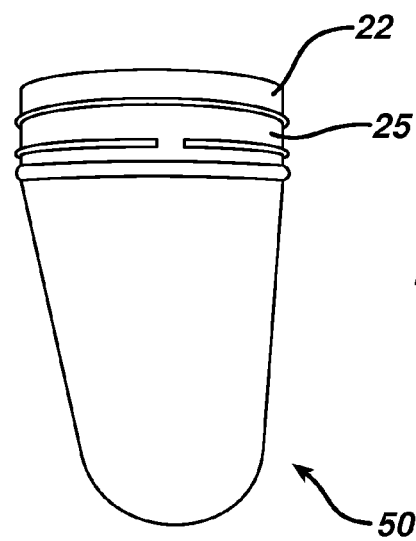
FIG. 11 is a side elevation of a preform useful in blow-molding the one-piece housing of FIG. 2.

The one-piece housing may be formed by blow-molding a thermoplastic preform to the desired final form. Those of ordinary skill in the art will recognize how to design the preform dimensions to result in the desired final form. For example, the one-piece housing 20 shown in FIG. 2 may result from blow-molding a thermoplastic preform 50 shown in FIG. 11. The preform 50 has elements of the rim 22, such as the groove 25, already molded into it. These elements are maintained during the blow-molding process.

The blow-molding process provides a one-piece housing having a substantially continuous exterior wall with an interior surface that is substantially smoothly continuous. Alternative molding processes include rotomolding. Again, these processes permit the formation of final housing shapes in which the projected area PA is symmetrical on opposite sides of one or more planes perpendicular to the rim 22, symmetrical about a center of the opening 21, and/or isotropic. In marked contrast to injection molding, the blow-molding process also permits the simple formation of desired one-piece housings having a projected area that is substantially larger than the rim. In cases in which the one-piece housing material is subjected to conditions that may potentially alter the dimensions of the opening and/or rim—structures that are significant to sealing engagement of the components of the device—it may be useful to incorporate structures to maintain these dimensions during the manufacturing process. For example, the process equipment may include elements that maintain the diameter of the rim after the formation of the preform, during the blow-molding process, and during a cool-down period after the one-piece housing is complete.

The unitary insert again includes a frame having disposed thereon electromechanical elements interconnected in an electrical circuit. The frame may be formed of one or more structural elements, preferably plastic, that may be formed by any means available. For example, one or more elements of the frame may be injection molded plastic components that form mounting surfaces for a motor or other motion-generating devices, a battery or other power sources, gears, shafts, etc. The frame may also have disposed thereon electrical connectors and one or more switches or switch elements. The individual components of the unitary insert are joined together to form the complete unitary insert. This is inserted through the single opening of the housing and attached thereto. As discussed above, the unitary insert 30 (such as shown in FIG. 4) may be inserted into the one-piece housing 20 using a single, linear motion. Alternatively, as shown in FIG. 6, the method may require that a distal portion 33' of the unitary insert be aligned with the opening, inserting the distal portion through the opening, pivoting the unitary insert to align a remaining portion of the unitary insert that has a projected area that is circumscribed by the rim, and inserting the remaining portion of the unitary insert through the rim.

Optionally, a gasket and/or damping member may be disposed between the unitary insert and the housing to further protect the electromechanical elements from the ingress of liquids and/or to inhibit the transfer of motion between the unitary insert and the housing.

The method also includes removably applying a cover to the housing to cover the opening thereof. In one embodiment, the cover is a cap, and the step of removably applying the cover comprises removably engaging the cap over the rim. In another embodiment, the cover is a plug, and the step of removably applying the cover comprises removably engaging the plug within the rim. If the cover is a plug, the method may include the step of arranging a gasket about the plug.

The unitary insert 30 is attached to at least one of the one-piece housing 20 and the cover 40 to provide a more robust device. The attachment may be permanent or it can be temporary or detachable. The attachment can be done through known methods including without limitation, welding, adhesives, and mechanically fastening (screw, snap, interference fit, and the like). In several preferred embodiments, the unitary insert is ultrasonically welded to either the cover or the one-piece housing.

The devices of the present invention can be used for any desired body-care regimen. Known regimens include cleansing, exfoliating, microdermabrasion, massage, and the like. In embodiments incorporating optional body-care elements, a user may select an appropriate body-care element, apply it to the exterior surface of the cover, apply water to the body-care element (if appropriate), activate the motion of the device, and apply the body-care element to desired locations. After use, the body-care element may be removed and discarded. Thus, the body-care elements may be in the form of pads, brushes, sponges, poufs (gathered nets of polymeric material), protrusions (for massaging, etc.), and the like.

Another method of the present invention relates to a method of making handheld electromechanical devices and/or permitting a user to select components of a handheld mechanical device body-care system. The method includes the steps of forming a one-piece housing defining a volume and having a single opening defined by a rim, selecting a unitary insert dimensioned to be insertable through the opening defined by the rim from a plurality of unitary inserts, inserting the selected unitary insert through the single opening of the housing and attaching the insert to the one-piece housing, selecting, from a plurality of covers, a cover arranged and configured to cooperate with the selected unitary insert, and removably applying the cover to close the single opening of the housing. Each of the plurality of unitary inserts includes a frame having disposed thereon electromechanical elements interconnected in an electrical circuit. Each of the plurality of different covers is arranged and configured to cooperate with one or more of the plurality of different unitary inserts.

The one-piece housing may be of any shape, or selected from among a plurality of shapes and sizes and surface features, as long as it is suitable for handheld, consumer use. Additionally, the plurality of unitary inserts may be selected from a supply of unitary inserts having different electromechanical elements, sizes, and/or shapes. Thus, the desired unitary insert may provide different motion, different power levels, and other different properties, as desired by consumers. The plurality of covers may be selected from a supply that are arranged and configured to cooperate with the various one-piece housings and unitary inserts. These covers may be caps, plugs, and the like, as described above.

Therefore, this method provides flexibility for manufacturers to provide customizable and/or a variety of handheld electromechanical devices on a single manufacturing line. Alternatively, it permits the creation of kits of body-care devices and inter-changeable elements for consumers to have a variety of customizable configurations in their homes.

As described above, at least two of the one-piece housing, unitary insert, and cover are preferably sealing engaged to resist the ingress of liquids into the one-piece housing. This may be achieved by arranging a gasket about the rim, about the cover, and/or between the unitary insert and the one-piece housing. In addition, the damping member described above may be provided between the unitary insert and the one-piece housing.

The kit having interchangeable components includes a first component that is a one-piece housing, a second component that is a unitary insert, and a third component that is a cover. The kit includes at least one of each of the first, second, and third components, and at least two of one of the components. Thus, the kit may include one one-piece housing and multiple unitary inserts and corresponding covers, or the kit may include one unitary insert and multiple one-piece housings and corresponding covers. While it may also be possible to have one cover and multiple one-piece housings and unitary inserts, this is likely to be rather uncommon. Finally, the kit may include a plurality of each of the three components.

Figure 12:
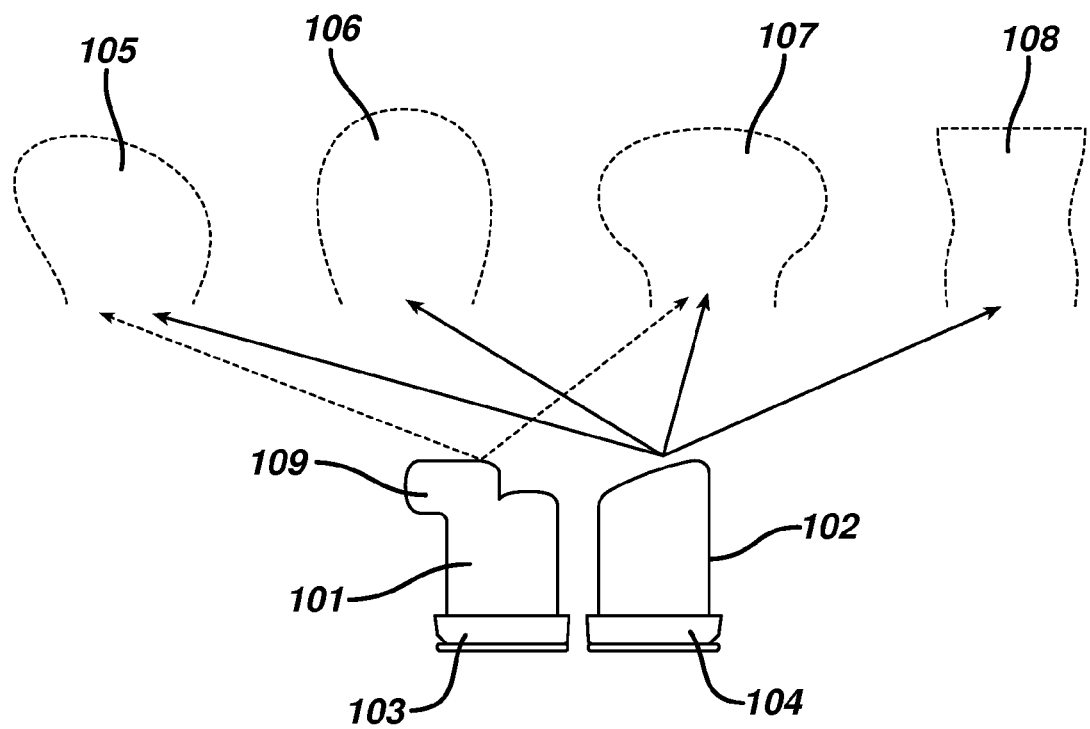
FIG. 12 is a schematic view of components of a kit comprising multiple unitary inserts and one-piece housings according to an embodiment of the present invention.

An example of a kit is shown in FIG. 12. The kit contains two unitary inserts 101, 102. Each unitary insert 101, 102 has associated therewith a cover 103, 104, respectively. The combination unitary insert/cover can be combined with one of four one-piece housings 105, 106, 107, 108 (shown in phantom cross-section). However, unitary insert 101 has a lateral extension 109 on its distal end, and this extension interferes with the two of the one-piece housings. Therefore, this unitary insert 101 can be used only with one-piece housings 105, 107 and not with one-piece housings 108, 109 (as indicated by the arrows connecting the unitary insert and housings).

The specification and embodiments above are presented to aid in the complete and non-limiting understanding of the invention disclosed herein. Since many variations and embodiments of the invention can be made without departing from its spirit and scope, the invention resides in the claims hereinafter appended.

The invention claimed is:

1. A method of making a handheld, electromechanical device useful in mammalian body-care, the method comprising:
   a) providing a one-piece housing having a continuous, seamless exterior wall with a single opening defined by a rim, wherein the rim circumscribes a rim area, and the one-piece housing has a projected area that is substantially larger than the rim area;
   b) providing a unitary insert dimensioned to be insertable through the opening defined by the rim, the unitary insert comprising a frame having disposed thereon electromechanical elements interconnected in an electrical circuit;
   c) inserting the unitary insert through the single opening of the one-piece housing;
   d) removably applying a cover having an exterior surface to close the opening of the one-piece housing; and
   e) attaching the unitary insert to at least one of the one-piece housing and the removable cover.

2. The method of claim 1, further comprising the step of sealingly engaging at least two of the cover, frame and one-piece unitary housing to resist the ingress of liquids into the one-piece housing.

3. The method of claim 1, wherein the one-piece housing has a shoulder, and the rim extends from the shoulder.

4. The method of claim 3, further comprising the step of arranging a gasket about the rim.

5. The method of claim 1, wherein the step of forming a one-piece housing comprises subjecting a thermoplastic preform to a blow-molding process to form the one-piece housing.

6. The method claim 1, wherein the step of forming a one-piece housing comprises rotomolding a polymeric material to form the one-piece housing.

7. The method of claim 1, wherein the one-piece housing has a projected area that is symmetrical on opposite sides of a plane perpendicular to the rim.

8. The method of claim 1, wherein the unitary insert has a projected area that is circumscribed by the rim, and inserting the unitary insert through the single opening involves a single, linear motion.

9. The method of claim 1, wherein the unitary insert has a projected area that extends outside of the opening, and inserting the unitary insert through the single opening comprises aligning a distal portion of the unitary insert with the opening, inserting the distal portion through the opening, pivoting the unitary insert to align a remaining portion of the unitary insert that has a projected area that is circumscribed by the rim, and inserting the remaining portion of the unitary insert through the rim.

10. The method of claim 1, further comprising providing a damping member between the unitary insert and the one-piece housing to inhibit the transfer of motion therebetween.

11. The method of claim 1, wherein the removable cover is arranged and configured to transmit at least one output of the electromechanical elements disposed within the one-piece housing through the exterior surface of the cover.

12. The method of claim 11, wherein the cover further comprises an aperture having a gasket and a moveable shaft disposed therein, and wherein the moveable shaft is operatively connected to the motor to transfer motion from the motor to a skin-contacting element disposed outside of the one-piece housing.

13. The method of claim 1, wherein the removable cover comprises a cap, and the step of removably applying the cover comprises removably engaging the cap over the rim.

14. The method of claim 1, wherein the removable cover comprises a plug, and the step of removably applying the cover comprises removably engaging the plug within the rim.

15. The method of claim 14, further comprising arranging a gasket about the plug.

16. The method of claim 1, further comprising arranging a gasket about the unitary insert between the unitary insert and the one-piece housing.

17. The method of claim 1, further comprising providing surface features on an outer surface of the one-piece housing.

18. The method of claim 1, wherein attaching the unitary insert comprises attaching the unitary insert to the one-piece housing after inserting the unitary insert through the opening.

19. A method of making a handheld, electromechanical device useful in mamalian body-care, the method comprising:
   a) forming a one-piece housing having a single opening defined by a rim, wherein the rim circumscribes a rim area, and the one-piece housing has a projected area that is substantially larger than the rim area;
   b) assembling a unitary insert dimensioned to be insertable through the opening defined by the rim, the unitary insert comprising a frame having disposed thereon electromechanical elements interconnected in an electrical circuit;
   c) inserting the unitary insert through the single opening of the housing;
   d) removeably applying a cover having an exterior surface to close the opening of the one-piece housing; and
   e) attaching the unitary insert to the cover prior to removably applying the cover to close the opening.

20. A method of making a handheld, electromechanical device useful in mammalian body-care, the method comprising:
   a) inserting a unitary insert through a single opening of a one-piece housing;
   b) removably applying a cover having an exterior surface to close the opening of the one-piece housing; and
   c) attaching the unitary insert to at least one of the one-piece housing and the removable cover so that said unitary insert is mechanically isolated from the one-piece housing to reduce transfer of undesired motion to the gripping surfaces of the one-piece housing;
   wherein:
   the one-piece is formed to have a continuous, seamless exterior wall with a single opening defined by a rim circumscribing a rim area and a projected area that is substantially larger than the rim area;

the unitary insert is dimensioned to be insertable through the opening defined by the rim; and the unitary insert is assembled by mounting on a frame the electromechanical elements of said electromechanical device interconnected in an electrical circuit to form a complete unitary insert.

21. The method of claim 20, wherein the one-piece housing is formed to have an interior surface that is substantially smoothly continuous so that the electromechanical elements are only mounted on the frame and cannot be mounted on the interior surface of the one-piece housing.

\* \* \* \* \*